United States Patent [19]

Benedikt et al.

[11] Patent Number: 5,341,696
[45] Date of Patent: Aug. 30, 1994

[54] PROCESS AND DEVICE FOR PRODUCING A PEEL OR TEAR TEST SPECIMEN ON A WELDED COMPOUND SHEET

[75] Inventors: Georg Benedikt, Schaffhausen; Werner Urech, Kaiserstuhl, both of Switzerland

[73] Assignee: Elpatronic AG, Zug, Switzerland

[21] Appl. No.: 41,939

[22] Filed: Apr. 2, 1993

[30] Foreign Application Priority Data

Apr. 3, 1992 [CH]  Switzerland .................. 01087/92
May 12, 1992 [CH]  Switzerland .................. 01522/92

[51] Int. Cl.$^5$ .................. G01M 19/00; B21D 28/10
[52] U.S. Cl. .................. 73/827; 73/835; 72/326; 225/1; 225/101
[58] Field of Search .................. 72/326, 325; 225/1, 225/94, 101, 100; 73/827, 833, 865.8, 864., 41, 864.42, 835

[56] References Cited

U.S. PATENT DOCUMENTS

| | | | |
|---|---|---|---|
| 2,674,123 | 4/1954 | Sooy .................. | 73/835 |
| 2,959,051 | 11/1960 | Simek et al. . | |
| 3,357,078 | 12/1967 | Moltchan .................. | 72/325 |
| 4,027,529 | 6/1977 | Olsen .................. | 73/827 |
| 4,030,650 | 6/1977 | Oberloier .................. | 225/100 |
| 4,292,852 | 10/1981 | Morris . | |
| 4,875,376 | 10/1989 | Fischer . | |

FOREIGN PATENT DOCUMENTS

| | | | |
|---|---|---|---|
| 52666 | 4/1979 | Japan .................. | 72/326 |
| 137820 | 10/1990 | Japan .................. | 225/100 |
| 804102 | 2/1981 | U.S.S.R. .................. | 72/326 |
| 1281324 | 1/1987 | U.S.S.R. .................. | 72/326 |
| 2241066 | 8/1991 | United Kingdom . | |

OTHER PUBLICATIONS

"Weldment evaluation methods" Defense Metals Information Center Report 244, Aug., 1968, J. J. Vagi, R. P. Meister, and M. D. Randall, pp. 32–45.

*Primary Examiner*—Daniel C. Crane
*Attorney, Agent, or Firm*—McCormick, Paulding & Huber

[57] ABSTRACT

A compound sheet with a welded seam is arranged on a table (2) of the device (1). By lowering a cutting and bending punch (4), a cutout is cut from the compound sheet and bent downwards. A pulling device is arranged inside the device (1) underneath the table (2) to seize the downwardly bent cutout and tear it off the compound sheet. The quality of the weld can be evaluated by visual inspection of the appearance of the rupture point, in a known manner. In this way, tear test specimens of consistent quality and informativeness can be prepared very quickly and easily.

14 Claims, 5 Drawing Sheets

PROCESS AND DEVICE FOR PRODUCING A PEEL OR TEAR TEST SPECIMEN ON A WELDED COMPOUND SHEET

BACKGROUND OF THE INVENTION

The invention relates to a process for producing a peel or tear test specimen on a welded compound sheet or part thereof. The invention also relates to a device for carrying out the process.

The joining together of sheets by welding, in particular by mash seam or laser welding, is known. The assembly constituted by the joined sheets is known as a compound sheet. To complete the quality inspection, compound sheets or parts thereof with the welded seam are regularly removed from the production process and the strength of the weld is tested by destruction of the compound sheet. This is done by making cuts in one of the two joined sheets with sheet-metal shears to expose a tongue of the sheet material. This cutout tongue is bent over and gripped by means of a slotted key. The key is turned and the tongue is wound on to the key, towards the welded seam. The key is turned until the material is destroyed. From the position and surface features of the rupture point in the tongue or in the weld, the quality of the welded seam can be judged by visual inspection by a suitably trained person.

The process which has been outlined here has been found to have a number of shortcomings. First, the process is relatively time-consuming, as the cutting and bending operations are performed separately, by hand. Second, it appears that the results obtained from the manual tearing or peeling by means of the said key can vary very considerably depending on how it is performed by the operator. This can make the ensuing visual appraisal of the weld difficult.

SUMMARY OF THE INVENTION

It is therefore the fundamental task of the invention to provide a process which does not possess the aforesaid disadvantages. In particular the process should allow a large number of peel or tear test specimens to be rapidly produced, and as near constant as possible conditions created for the actual peeling or tearing operation.

This is accomplished in a process of the kind stated at the outset, by forming a cutout in the compound sheet by means of a cutting and bending element which defines the dimensions of the cutout, and by coupling the cutout to a device which exerts on the cutout a defined tension acting via the cutout on the welded seam.

By making the cutout by means of a cutting and bending element, controlled conditions are created in this working operation, and this is beneficial to the ensuing peeling or tearing stage. Moreover a large number of test pieces can be prepared quickly in this way, even by semi-skilled operating personnel. The ensuing step of pulling with defined force ensures that the pulling operation cannot exert any influence giving rise to an incorrect evaluation.

In one way of carrying out the process, the compound sheet is secured on a table during the cutting and bending operation. During the ensuing tearing or peeling of the cutout, however, the compound sheet is able to move freely on the table. The cutout is torn or peeled off over a rounded edge of the table. These arrangements prevent the table from influencing the condition of the specimen.

In another way of carrying out the process, the specimen is securely clamped to the table during the pulling operation, and the edge of the table is not rounded, but square; this assists peeling.

A preferred test specimen geometry is obtained by forming the cutout as a cutout extending to the welded seam, the cuts forming its side edges being angled at approximately 15° to the perpendicular to the welded seam. The cuts terminate approximately 5 mm from the welded seam, at which point the cutout is bent downwards.

The invention also has the underlying task of providing a device to carry out the process.

BRIEF DESCRIPTION OF THE DRAWINGS

Embodiments of the invention will now be explained in detail by way of example and with reference to the drawings.

DESCRIPTION OF THE PREFERRED EMBODIMENTS

Figure 1:
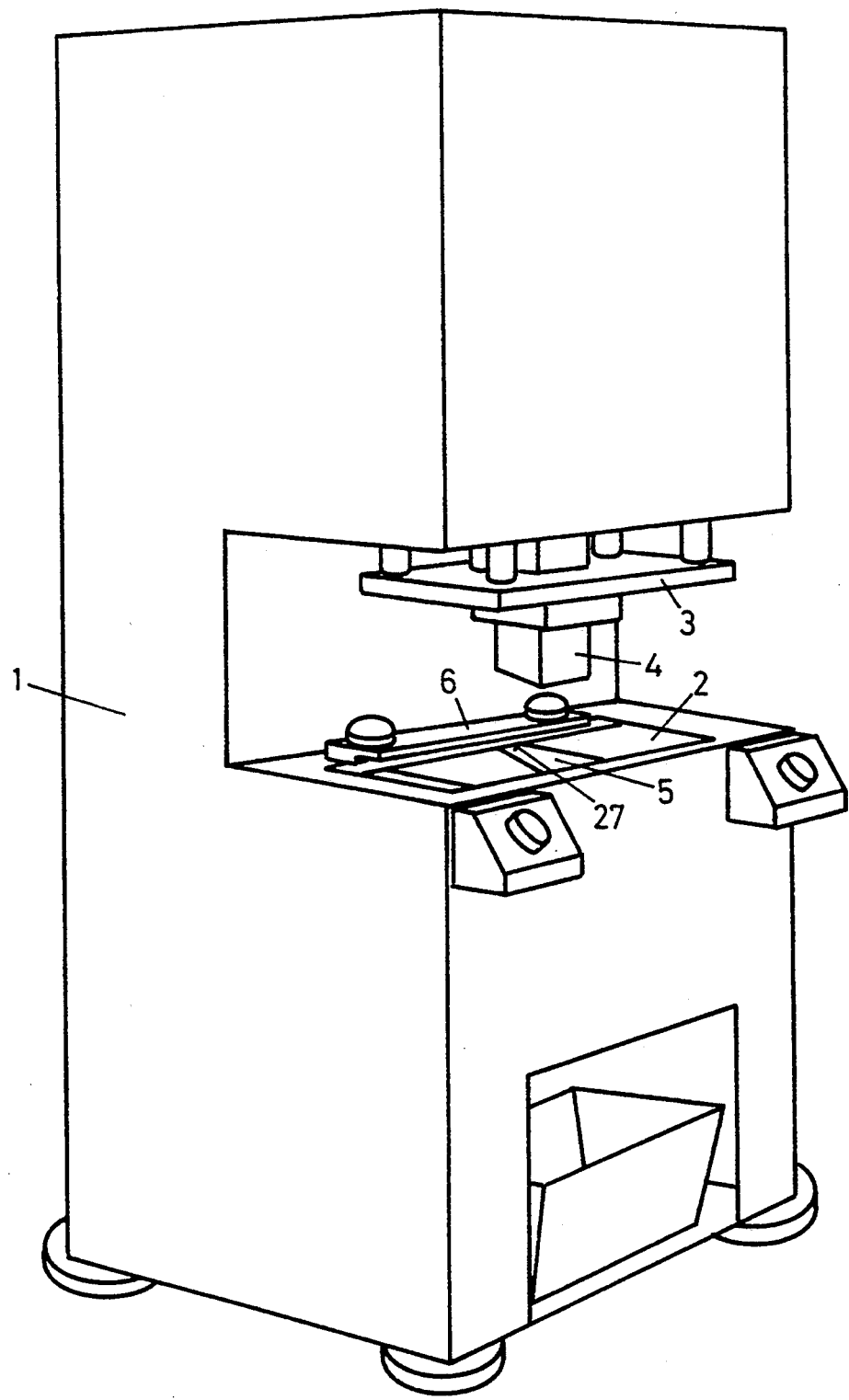
FIG. 1 shows an exterior view of a device for carrying out the process.
Figure 2:
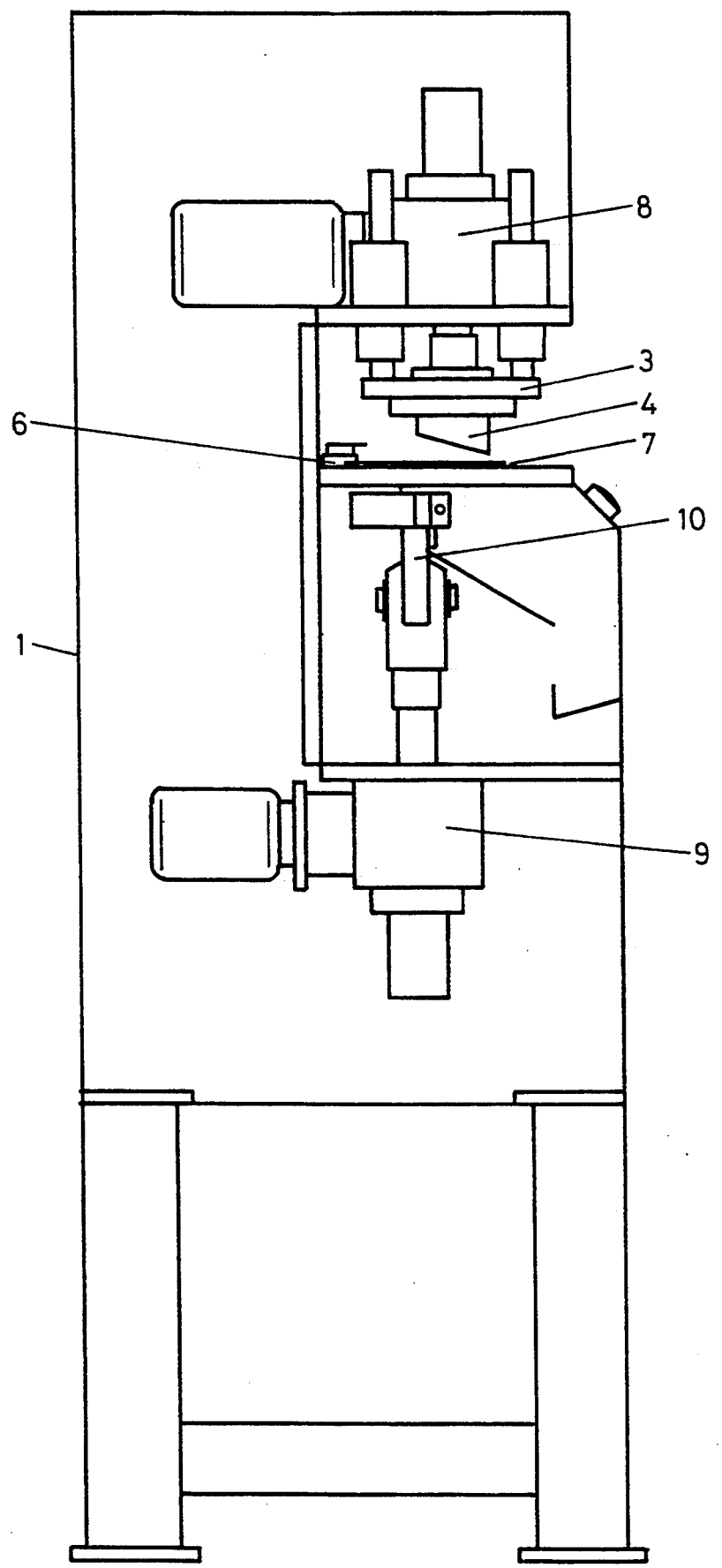
FIG. 2 shows a first vertical section through the device of FIG. 1.
Figure 3:
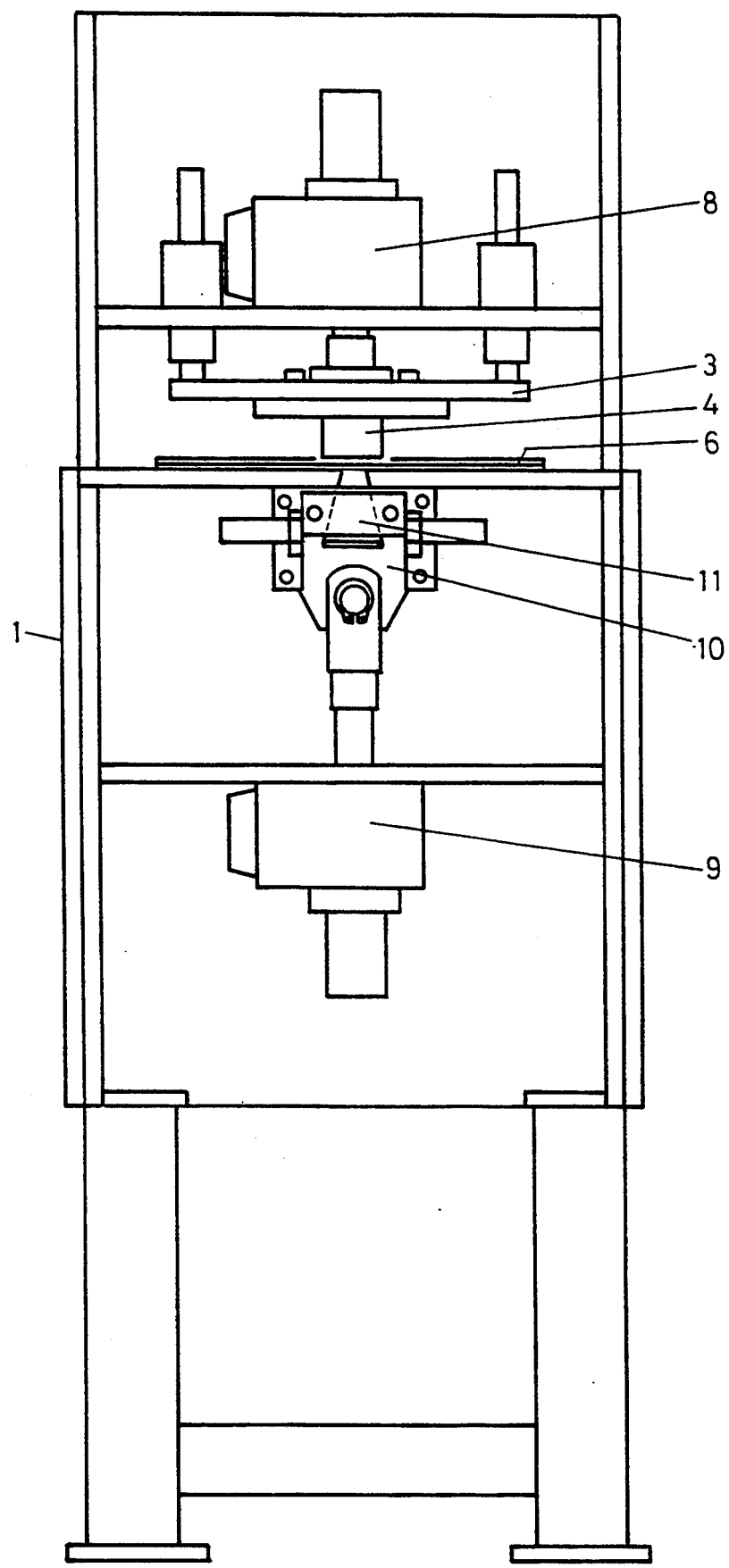
FIG. 3 shows a second vertical section through the device of FIG. 1.

FIG. 1 shows a device 1 for carrying out the process of the invention. The device 1 has a table 2. A presser plate 3 which carries a cutting and bending punch 4 is arranged above the table 2. The presser plate together with the cutting and bending punch 4 can be moved towards and away from the table by an actuating unit 8 (FIG. 2). The compound sheet or part thereof is placed on the table 2, which has an opening 5 for the cutting and bending punch. An adjustable stop 6 is provided for aligning the compound sheet or part thereof. The stop 6 enables the compound sheet or part thereof to be located with the welded seam parallel with, or at an oblique angle to, the long side of the table. An actuating unit 9 for a grab plate 10, which catches the cut and bent cutout of the compound sheet, as will be explained in detail presently, is provided under the table 2. The table 2 also has a holder arrangement (not shown) for the compound sheet or part thereof. This holder arrangement may consist, for example, of electromagnets arranged beneath the table plate, or of a mechanical holding-down clamp.

Figure 4:
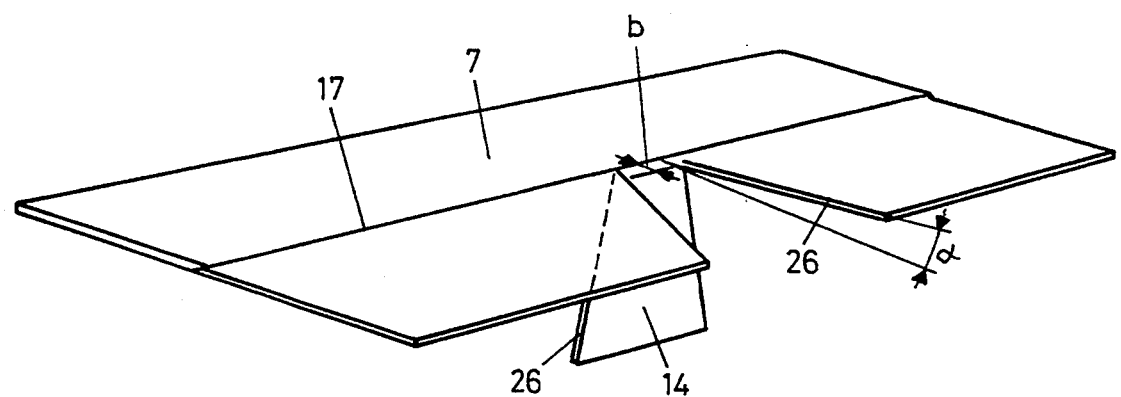
FIG. 4 is a view of a part of a compound sheet which has been cut and bent.

To carry out the process, a flat compound sheet or part thereof 7 (FIG. 4) is placed on the table 2 and pushed up to the preset stop 6. The compound sheet part 7 is then secured by the holder arrangement. The cutting and bending punch is propelled downwards and cuts from the compound sheet a cutout conforming to the shape of the punch and bends this cutout downwards below the plane of the table (the opening 5 in the table is provided for this purpose). The result of this first step of the process is a compound sheet part 7 with a downwardly bent cutout 14 as shown in FIG. 4. The compound sheet part 7 shown in FIG. 4 comprising the two sheets joined by the welded seam 17 is merely a preferred embodiment illustrated by way of example. In particular a laser welded butt joint may be made in place of the mash seam weld shown in the drawing. In the illustrated example, the cutout 14 is formed by the cutting and bending punch 4 with the cuts 26 converging in the direction towards the welded seam 17. Each of the cuts 26 forms an angle a of approximately 15° with the perpendicular to the welded seam. The cutout 14 extends to the welded seam and is bent down at a distance b from the welded seam 17 of approximately 5 mm.

The shape of the cutout 14 which has been described has the particular advantage that it enables the cutout 14 to be seized in a simple manner by the grab plate 10 arranged underneath the table, for the next stage of the process. The grab plate 10 grips the cutout 14 while the cutting and bending punch 4 is being raised above the table plate 2 and while the compound sheet part 7 continues to be held secure by the holder arrangement. After the grab plate 10 has seized the cutout 14, the holder arrangement is released, and the compound sheet part 7 rests freely on the table 2. The cutout 14 is then pulled downwards by means of the grab plate 10 until the cutout 14 or the weld 17 is destroyed. In order that the rear edge 27 of the table opening 5 should not influence the result, this edge 27 is rounded, and the compound sheet part 7 rests freely, as stated, on the table 2. After destruction of the cutout 14, the remainder of the compound sheet 7 is removed from the device 1 and the rupture point is visually examined in a known manner to check the quality of the weld.

In another embodiment the cutout 14 is held securely on the table, preferably by a mechanical holding-down clamp, during destructive testing. Also, the side of the table is sharp-edged and supports the specimen close to the seam, i.e. on the side opposite the tongue. This ascertains the maximum peeling component.

Figure 5:
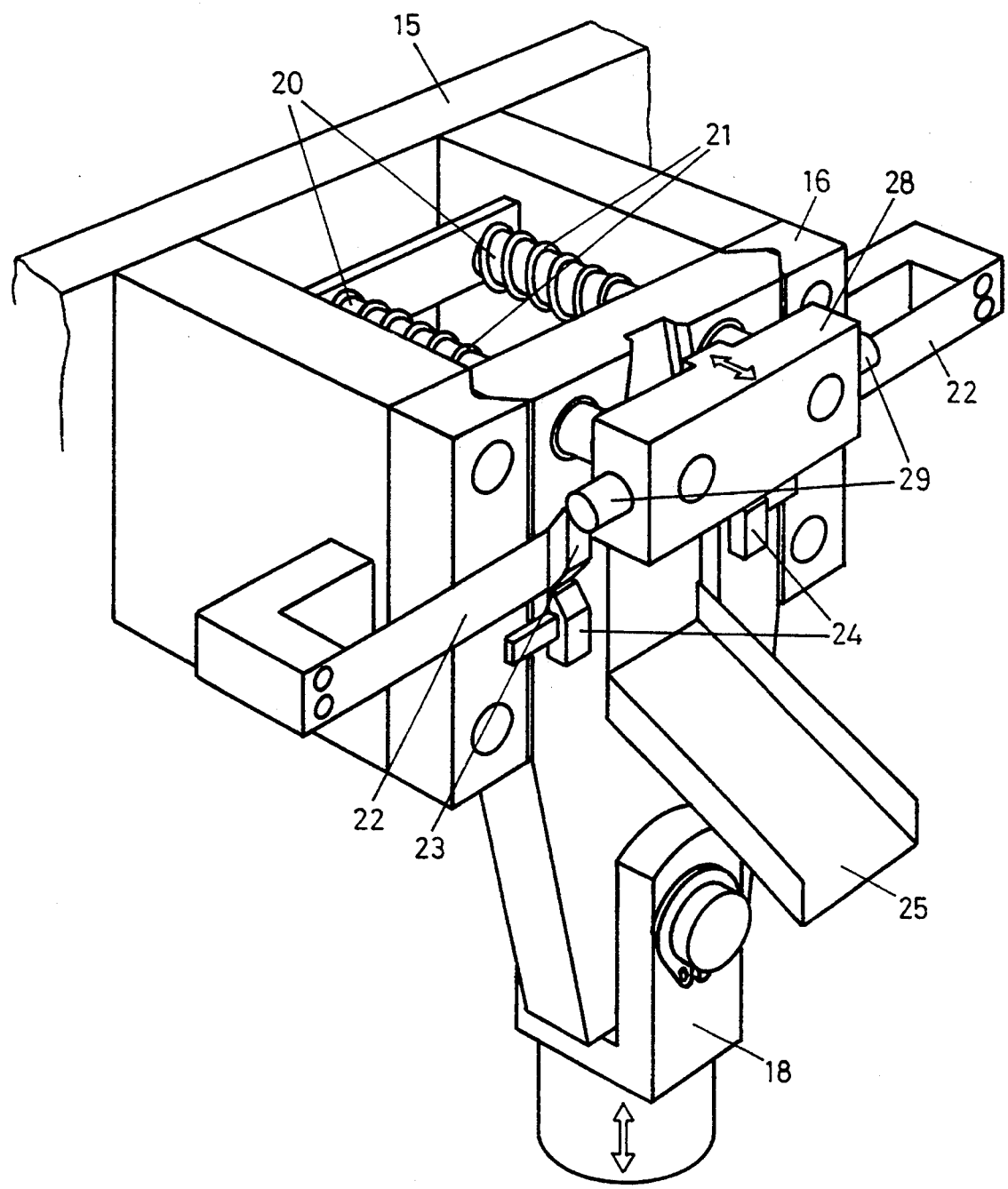
FIG. 5 is a partial view of the pulling device of FIG. 1.

FIG. 5 shows the grab plate 10 and its sliding guide 16, which is fixed to the machine frame 15 of the device 1. The grab plate 10 is connected to the actuating unit 9 by means of the clevis 18, allowing it to be moved up and down. The actuating unit 9 and the actuating unit 8 may each be provided with pneumatic, hydraulic or electric motor drive systems. When the grab plate 10 is raised towards the table 2 to grip the cutout 14, the pressure jaw 28 is lifted off by the grab plate 10 to allow the cutout 14 to pass between the grab plate and the pressure jaw. The lifting off of the pressure jaw 28, which is attached to the grab plate 10 by means of guide pins 20 fitted with compression springs 21, is effected by means of control pieces 23 each of which is contacted by a spigot 29 of the pressure jaw, causing the latter to be lifted away from the grab plate 10 against the action of the compression springs 21. At the end of the upward stroke the spigots 29 are no longer acted on by the control pieces 23, so that the pressure jaw 28 is pressed against the grab plate 10 by the compression springs 21, causing the cutout 14 to be inserted into the matching recess 11 in the grab plate 10. The cutout 14 is held by the shape of the recess 11 in the grab plate 10 and by the pressure jaw 28. When the grab plate 10 is lowered, the cutout 14 is then torn or peeled off the compound sheet part 7 in the manner which has already been described. As the grab plate 10 and pressure jaw 28 move downwards the spigots 29 engage underneath the upper forward edge of the control pieces 23. As these control pieces 23 are mounted on leaf springs 22, they can be deflected out of the way of the spigots 29 as the downward movement continues. The pressure jaw 28 is therefore not opened at the start of the downward movement and keeps a firm hold on the cutout 14 so that the tearing or peeling can be performed. After the downward travel necessary for the destruction of the test specimen has been effected, the spigots 29 impinge on fixed control pieces 24 which cause the pressure jaw to open against the action of the compression springs 21. This opening of the pressure jaw 28 releases the parted cutout 14, which can be discharged to a container via a chute 25. If the cutout 14 is also needed for the evaluation of the weld 17, it can then be recovered from the container. In this case, it is also advantageous if the compound sheet and the cutout 14 are marked before or simultaneously with the cutting and bending operation so that a cutout can be linked to the corresponding compound sheet after it has been severed from it.

Figure 6:
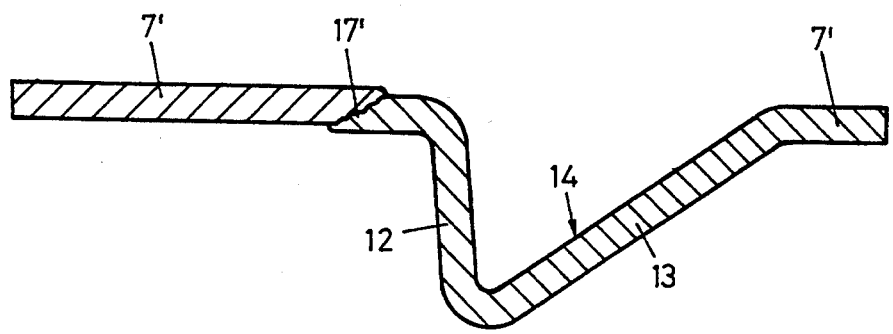
FIG. 6 shows a vertical section through another cut and formed tear test specimen.

FIG. 6 shows another form of cutout which can be produced in the compound sheet 7' by the cutting and bending operation of the cutting and bending punch 4. In this form, the forward edge of the cutout 14 remains attached to the compound sheet 7'. The cutout 14 is cut away from the compound sheet 7' at the sides only and is shaped as seen in FIG. 6, with a steeply downwardly bent first cutout portion 12 and a connecting gently downwardly bent second cutout portion 13. With this configuration of cutout 14 the second stage of the process, the tearing or peeling off of the cutout 14 from the compound sheet 7', can be performed by making the cutting and bending punch 4 descend further after the cutting and bending operation so that it acts as a pulling device. The continued descent of the cutting and bending punch 4 exerts a pulling force on the first cutout portion 12 in the direction of the weld seam 17', which in turn causes the destruction of the cutout 14 or weld seam 17'. In this configuration of the process the pulling device arranged under the table 2 can be dispensed with. Alternatively, instead of using the cutting and bending punch to perform the peeling operation, this can be performed with a separate tearing or peeling punch, which may be shaped differently if the need arises.

We claim:

1. Device for carrying out the process of producing a peel or tear test specimen on a welded compound sheet or part thereof characterized by a table to support the compound sheet or part thereof, an actuating device, a cutting and bending punch arranged above the table and connected to the actuating device to produce a cutout in the compound sheet or part thereof and pulling means arranged underneath the table for gripping and exerting a defined tension on the cutout.

2. Device according to claim 1, characterized in that the table (2) has an opening (5) for the cutting and bending punch (4), with an edge on the bend side (27) which is rounded or sharp-edged.

3. Device according to claim 1, characterized in that the table (2) has an adjustable stop (6) and a releasable holder for the compound sheet or part thereof.

4. Device according to claim 1, characterized in that the pulling means has a convergent recess (11) intended to receive the cutout (14).

5. Device for carrying out the process of producing a peel or tear test specimen on a welded compound sheet or part thereof characterized by a table to support the compound sheet or part thereof, an actuating device arranged above the table, and a cutting, bending and pressing punch which is propelled by the actuating device onto the compound sheet in a cutting and bending operation to form a cutout in the shape of a seat, the actuating device having a displacement sufficient to cause the punch to additionally exert a pulling and tearing force on the cutout which results in destruction of the specimen.

6. Process for producing a peel or tear test specimen on a welded compound sheet or part thereof having a welded seam, characterized by forming a cutout in the compound sheet by means of a cutting and bending element which defines the dimensions of the cutout, and coupling the formed cutout to a tensioning device and thereby exerting on the cutout a defined tension acting through the cutout on the welded seam.

7. Process according to claim 6 further characterized by arranging the compound sheet or part thereof on a table having an opening for the cutting and bending element, fixing the compound sheet or part thereof to the table during the forming step, and resting the compound sheet or part thereof essentially freely on the table during the step of exerting a defined tension.

8. Process according to claim 6 characterized by fixing the compound sheet or part thereof to a table with an opening for the cutting and bending element during the cutting, bending and exerting.

9. Process according to claim 8 characterized in that during the exerting step the cutout is pulled over a rounded edge of the opening in the table.

10. Process according to claim 8 characterized in that during the exerting step the cutout is pulled over a sharp edge of the opening in the table.

11. Process according to claim 6 characterized in that during the step of forming, a cutout extending to the welded seam is formed.

12. Process according to claim 11 characterized in that during the step of forming the cutout is formed by two cuts, each cut angled at approximately 15° to the perpendicular to the welded seam.

13. Process according to claim 11 characterized in that during forming the cutout is bent at a location approximately 5 mm from the welded seam.

14. Process according to claim 6 characterized in that during forming the cutting and bending element forms a cutout (14') constituting a seat (12,13) for the element, and during exerting the cutting and bending element is lowered further onto the compound sheet or part thereof to exert tension acting in the direction of the welded seam.

* * * * *